(12) United States Patent
Molitoris et al.

(10) Patent No.: US 8,951,978 B2
(45) Date of Patent: Feb. 10, 2015

(54) MATERIALS AND METHODS FOR TREATING DISEASES CAUSED BY GENETIC DISORDERS USING AMINOGLYCOSIDES AND DERIVATIVES THEREOF WHICH EXHIBIT LOW NEPHROTOXICITY

(75) Inventors: Bruce A. Molitoris, Indianapolis, IN (US); David M. Bedwell, Birmingham, AL (US); Ruben M. Sandoval, Indianapolis, IN (US)

(73) Assignee: Indiana University Research and Technology Corp., Indianapolis, IN (US)

( * ) Notice: Subject to any disclaimer, the term of this patent is extended or adjusted under 35 U.S.C. 154(b) by 0 days.

(21) Appl. No.: 13/315,190

(22) Filed: Dec. 8, 2011

(65) Prior Publication Data

US 2012/0157398 A1 Jun. 21, 2012

Related U.S. Application Data

(60) Division of application No. 12/473,877, filed on May 28, 2009, now abandoned, which is a continuation of application No. PCT/US2007/085974, filed on Nov. 29, 2007.

(60) Provisional application No. 60/867,671, filed on Nov. 29, 2006.

(51) Int. Cl.
*A61K 31/70* (2006.01)
*A61K 31/7034* (2006.01)

(52) U.S. Cl.
CPC .................................. *A61K 31/7034* (2013.01)
USPC .......................................................... 514/40

(58) Field of Classification Search
None
See application file for complete search history.

(56) References Cited

U.S. PATENT DOCUMENTS

| 3,091,572 | A | 5/1963 | Luedemann et al. |
| 3,163,704 | A | 6/1964 | Charney |
| 3,651,042 | A | 3/1972 | Marquez et al. |
| 5,840,702 | A | 11/1998 | Bedwell |
| 6,475,993 | B2 * | 11/2002 | Tremblay ........................ 514/37 |

FOREIGN PATENT DOCUMENTS

WO WO 2004-105688 A2 12/2004

OTHER PUBLICATIONS

Sandoval et al., J. Am Soc. Nephrol, 17, 2006, pp. 2697-2705.*
International Searching Authority, International Search Report for PCT/US07/85974, issued Aug. 2008.
International Searching Authority, Written Opinion for PCT/US07/85974, issued Aug. 2008.
International Searching Authority, International Preliminary Report on Patentability for PCT/US07/85974, issued Jun. 2009.
Sandoval, R.M., et al., "A Non-Nephrotoxic Gentamicin Congener that Retains Antimicrobial Efficacy," J. Am Soc. Nephrol 17, pp. 2697-2705, 2006.

* cited by examiner

*Primary Examiner* — Traviss C McIntosh, III
(74) *Attorney, Agent, or Firm* — Faegre Baker Daniels LLP

(57) ABSTRACT

Various aspects related to the preparation of congeners of the aminoglycosides gentamicin such as the congener C2 and using this compound or derivatives thereof and pharmaceutically active salts to treat diseases that involve genetic mutations which introduce a missense or premature stop codon into a gene. Still other aspects include treating human or animal patients with the gentamicin congener C2 and derivatives and pharmaceutical salt thereof to overcome, or to at least mitigate, the symptoms of disease and disorders such as some forms of Becker's or Duchenne muscular dystrophy, Hurler's Syndrome and Cystic Fibrosis that have as their etiology the presence of a premature stop codon in a gene whose proper expression is necessary for good health.

4 Claims, 19 Drawing Sheets

MATERIALS AND METHODS FOR TREATING DISEASES CAUSED BY GENETIC DISORDERS USING AMINOGLYCOSIDES AND DERIVATIVES THEREOF WHICH EXHIBIT LOW NEPHROTOXICITY

PRIORITY CLAIM

This application is a divisional application of U.S. utility patent application Ser. No. 12/473,877, filed on May 28, 2009, which is a continuation of PCT/US07/85974, filed Nov. 29, 2007 which claims the benefit of U.S. provisional patent application No. 60/867,671 filed on Nov. 29, 2006, each of which is incorporated herein by referenced in its entirety.

STATEMENT OF GOVERNMENTAL RIGHTS

This invention was made with government support under grant number DK061594 awarded by the National Institutes of Health. The government has certain rights in the invention.

FIELD OF THE INVENTION

Various aspects relate generally to materials and methods for treating diseases caused by genetic disorders that include the imposition of a premature stop codon within a gene. These materials and methods include the use of aminoglycosides that exhibit reduced cytotoxicity.

BACKGROUND

There are a number of monogenetic diseases, including genetic mutations that introduce a premature stop codon into a gene, resulting in either no gene product or in a gene product made by expressing the gene that is either wholly or partially inactive. Such diseases include, for example, Duchenne Muscular Dystrophy (DMD), Cystic Fibrosis (CF), and may well include some genetic mutations which lead to the development of various cancers.

Duchenne Muscular Dystrophy (DMD) is due to the mutation of a gene in the X chromosome coding for a protein called dystrophin. The mutations of the dystrophin protein vary from one family of patients to another, but it always results in the absence of a functional dystrophin protein under the membrane on the muscle fiber. The absence of the dystrophin protein increases the vulnerability of the muscle fibers during contraction. Accordingly, repeated cycles of contraction and relaxation of the muscle produces a progressive reduction of the number of muscle fibers. The end result is a loss of strength which confines many patients to a wheel chair by the age of ten and in many cases to premature death in their early twenties.

Roughly 70% of the mutations of the dystrophin gene are large deletions of one of several exons, Still other mutations are small point mutations due either to a small deletion of a few base pairs leading to a shift of the reading frame, or changes of only one base pair producing a missense or a stop codon within the gene. It is estimated that about 5% of all DMD mutations may be due to premature stop codons in the gene.

Cystic fibrosis (CF) is due to a mutation of a gene coding for the CF transmembrane conductance regulator (CFTR) protein. Experiments with a bronchial epithelial cell line obtained from a CF patient having a premature stop mutation in the CFTR gene having confirmed this hypothesis. This mutation results in a premature end of the synthesis of the CFTR protein and thus is a non-functional protein. Early attempts to address this condition included treating these cells with aminoglycoside antibiotics G418 (100 mg/ml) or with gentamicin (200 mg/ml) for about 18 to 24 hours. Incubation with gentamicin suppressed the premature stop mutation by enabling the ribosome to insert an amino acid at the premature stop codon. Accordingly, a full-length CFTR protein is produced. The suppression of the premature stop codon by gentamicin is thought to be mediated by mis-pairing between the stop codon and a near-cognate aminoacyl tRNA. Furthermore, work has demonstrated that the full length CFTR protein resulting from the incubation with the aminoglycoside antibiotics is present in the cell membrane and is functional.

The mdx mouse is an animal model for DMD. The mouse's gene includes a point mutation in the dystrophin gene resulting in a truncated protein which is not incorporated in the muscle fiber membrane. Accordingly, this animal model presents an opportunity to test the effect of various compounds that promote readthrough of premature stop codons for their effect on masking the defect. For additional reading on the causes of some forms of DMD and cystic fibrosis and attempts to treat these diseases using gentamicin, please see U.S. Pat. No. 6,475,993, which is incorporated by reference herein in its entirety.

One strategy put forward to treating diseases of this nature is to provide a medicant that enables readthrough of premature stop codons; One such class of drugs with this capacity is the widely-used antibiotics referred to as aminoglycosides. While these drugs may have the potential to provide treatment for such disorders, they have a serious problem in that many, if not all of them, including the natural occurring form of gentamicin exhibit severe nephrotoxicity and/or ototoxicity. Accordingly, most naturally-occurring aminoglycosides cannot be prescribed on a daily basis for the lifetime of the patient without heightening the risk of acute kidney failure or inner ear toxicity.

Given the devastating effects that these various diseases have on the individuals afflicted with them, and the lack of treatments available for these diseases, there is a compelling need for various methods and materials which can be used to treat these diseases. Various aspects of the following disclose detail materials and methods for addressing this need.

BRIEF SUMMARY

One embodiment includes using the C2 congener of gentamicin or a derivative and/or pharmaceutically-acceptable form thereof to treat monogenetic diseases.

In one embodiment, the disease treated is selected from the group consisting of Duchenne muscular dystrophy (DMD), Cystic Fibrosis, Becker's muscular dystrophy, Hurler's Syndrome, or any monogenetic disease secondary to a premature stop codon.

Another embodiment includes isolating the C2 congener of the aminoglycosides gentamicin for use in the treatment of pathologies whose etiology includes the occurrence of a premature stop codon in a gene.

Still another embodiment includes using derivatives of the C2 congener and or pharmaceutically acceptable salts of the C2 congener or derivatives thereof which exhibit low nephrotoxicity to treat monogenetic diseases.

One aspect is a method of treating genetic disorders that involves the imposition of a stop codon in the middle of an otherwise functional gene while providing a patient the medication in the form of the C2 congener of gentamicin which has reduced the nephrotoxicity.

Still another embodiment includes the use of mixtures of various congeners of gentamicin and/or native gentamicin to produce formulations that have advantageous medicinal effects. In one such embodiment the congener C2 is mixed with native gentamicin to produce a formulation that is less toxic than native gentamicin, and has a larger effect on stop codon readthrough than C2 congener alone.

In still another embodiment, the method involves administering a therapeutically-effective dose of a congener of gentamicin such as C2 or a pharmaceutically-acceptable salt thereof.

Yet another embodiment includes administering a therapeutically effective dose of a mixture of congeners of gentamicin such as C2 and at least one other congener or a portion of native gentamicin and or a pharmaceutically acceptable salt thereof to a human or animal patient for the treatment of a disease or condition.

One aspect is a composition for promoting readthrough of a stop codon, comprising an isolated and purified compound having the following formula (C2 in formula 1), or a pharmaceutically acceptable salt thereof:

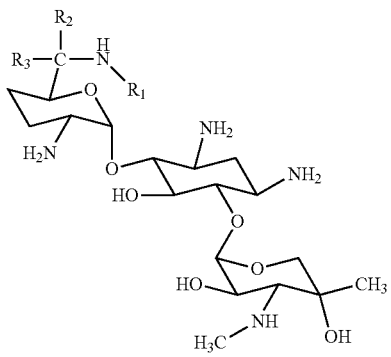

wherein $R_1$ and $R_3$ are H, and $R_2$ is $CH_3$ this compound may be referred to as C2 in Formula 1.

In one embodiment the compounds, C2 in Formula 1, is suitable for promoting readthrough of a stop codon selected from the group consisting of: UAA, UGA and UAG. In still another embodiment the compound shown as C2 in Formula 1 is suitable for promoting readthrough of a stop codon having the sequence UAG.

Still another embodiment is a method for promoting readthrough of a stop codon, comprising the steps of: identifying a nucleic acid included in a system for RNA translation, wherein said nucleic acid includes a stop codon; and providing an isolated and purified compound C2 in Formula 1, or a pharmaceutically acceptable salt thereof, and administering the compound an in an amount sufficient to promote readthrough of the stop codon in the nucleic acid.

Yet another aspect is a method of treating a genetic disease or disorder, comprising the steps of: identifying a patient, wherein the patient has a pathology including the imposition of a premature stop codon in the open reading frame of an otherwise functional gene; and administering a therapeutically effective dose of an isolated and purified compound having the formula, shown as C2 in Formula 1 or a pharmaceutically acceptable salt thereof. In one embodiment the herein genetic disease treated in this manner is selected from the group comprising: some forms of Duchenne Muscular Dystrophy, cystic fibrosis, Hurler's Syndrome, and Becker muscular dystrophies. In one embodiment the patient is a human. In still another embodiment the patient is an animal.

Yet another embodiment is a method of treating a genetic disease, comprising the steps of: identifying a patient, wherein the patient exhibits a pathology that includes the imposition of a premature stop codon in to the open reading frame of an otherwise functional gene; and formulating a mixture of a therapeutically effective dose of an aminoglyoside enriched in an isolated and purified compound having the formula. Shown as C2 in Formula 1, or a pharmaceutically acceptable salt thereof: wherein the compound is present in said formulation at a level sufficient to reduce the cellular toxicity of the aminoglyoside; and administering a therapeutically effective dose of said formulation to the patient.

Another embodiment is a kit for promoting readthrough of a stop codon, comprising: an isolated and purified compound having the formula shown as C2 in Formula 1. In one embodiment the kit is used to promote readthrough under in vitro conditions in still another embodiment the kit is used to promote readthrough under in vivo conditions.

One embodiment the compound having the formula designated at C2 in Formula 1 is used to promote readthrough of at least one sequence including at least one stop codon selected from the group comprising UAGC, UAAC, UGAC, UAAG, UAGG, UGAG, UAAU, UAGU, UGAU, UAAA, UAGA, and UGAA.

DESCRIPTION

Figure 1A:
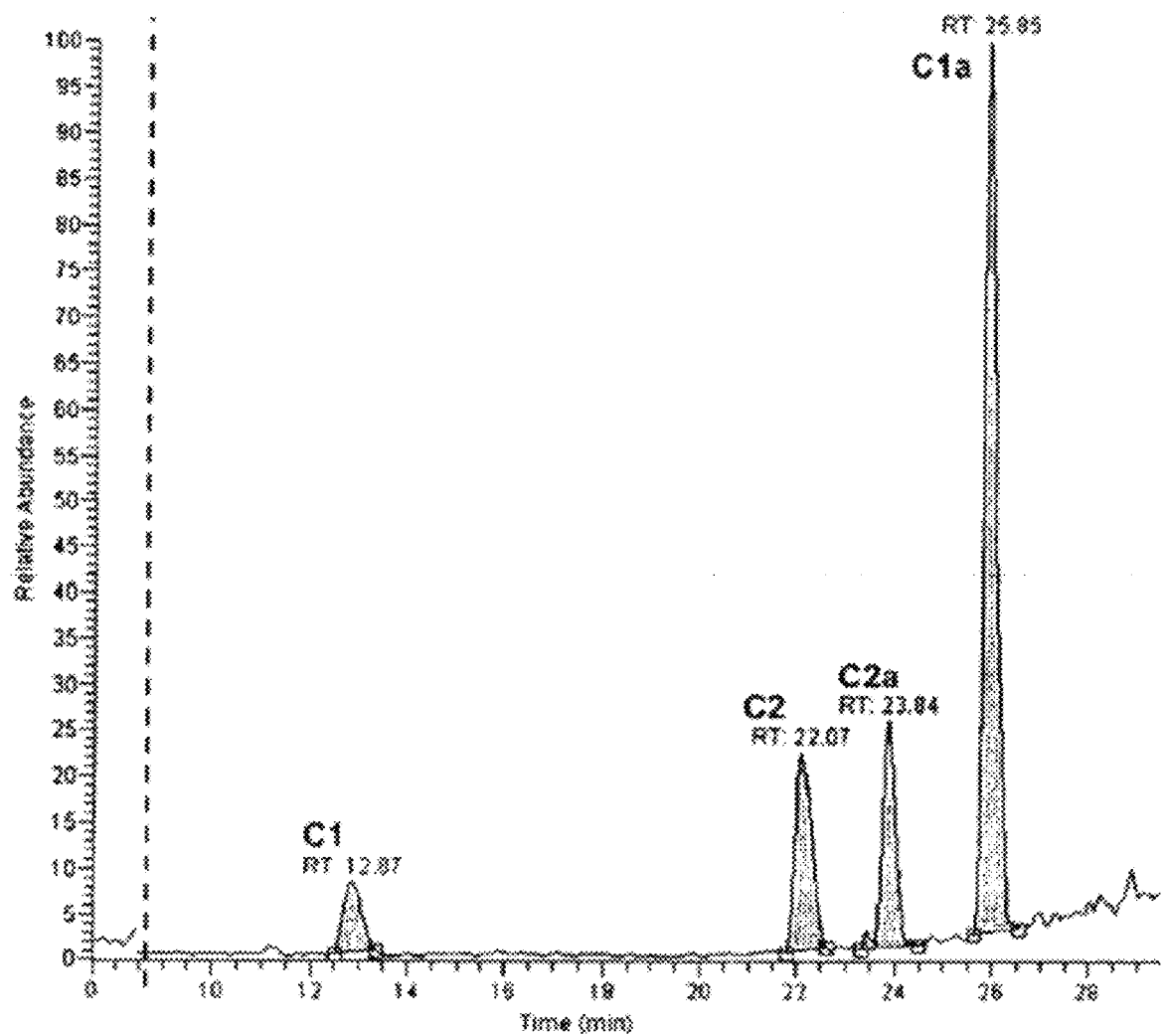
FIG. 1. Using HPLC techniques, individual congeners of gentamicin, including the enantiomers C2 and C2a were separated with no apparent cross-contamination.

For the purposes of promoting an understanding of the principles of the disclosure, reference will now be made to the embodiments illustrated herein and specific language will be used to describe the same. It will nevertheless be understood that no limitation of the scope of the disclosure is thereby intended. Any alterations and further modifications in the described processes, systems or devices, and any further applications of the principles of the disclosure as described herein, are contemplated as would normally occur to one skilled in the art to which the invention relates.

DEFINITIONS

Unless noted otherwise terms are given their usual and customary meaning in the art to which the disclosure pertains.

The expression "gentamicin complex" or "native gentamicin complex" or "native gentamicin" used herein includes commercially available mixture that includes at least two of at least the 4 congeners of gentamicin disclosed herein.

The expression "consisting essentially of," as used herein in reference to the gentamicin $C_2$ and/or gentamicin $C_{2a}$-containing compositions, is intended to signify that such composition may contain trace amounts of the $C_1$ and/or $C_{1a}$ gentamicin congeners, but that such amounts are less than that which would give rise to clinically significant nephrotoxicity. For example, the permissible amount of gentamicin $C_1$ and/or $C_{1a}$ per dose in the composition in some embodiments is generally about 5% by weight, or less, and preferably less than 1% by weight.

The free base, as well as pharmaceutically acceptable acid addition salts of the gentamicin described herein can be employed in the practice of various aspects of the disclosure. The expression 'pharmaceutically acceptable acid addition salt" is used herein to refer to a mono or poly salt formed by the interaction of one molecule of the gentamicin congener C2 with one or more moles of a pharmaceutically acceptable acid. Included among those acids are acetic, hydrochloric, sulfuric, maleic, phosphoric, nitric, hydrobromic, ascorbic, malic and citric acid, and those other acids commonly used to make salts of amine-containing pharmaceuticals. Hydrophobic acids, such as fatty acids having at least eight carbon atoms, provide salts of reduced solubility. Salts of the gentamicin component used in the practice of this invention with pharmaceutically acceptable acids are suitable for incorporation in a solution or suspension formulation, using a pharmaceutically acceptable carrier.

As used herein, the term "pharmaceutically acceptable carrier" includes any and all solvents, diluents, or other liquid vehicle, dispersion or suspension aids, surface active agents, isotonic agents, thickening or emulsifying agents, preservatives and the like, as suited to the particular dosage form desired. Remington's Pharmaceutical Sciences, 20th Edition, A. R. Gennaro (Williams and Wilkins, Baltimore, Md., 2000) discloses various carriers used in formulating pharmaceutical compositions and known techniques for the preparation thereof. Except, insofar as any conventional carrier medium is incompatible with the compositions used to practice various aspects of the disclosure, such as by producing any undesirable biological effect, its use is contemplated to be within the scope of this disclosure. Thus, solutions or suspensions of the gentamicin component described herein can also include a sterile diluent, such as water for injection, saline solution, fixed oils, polyethylene glycols, glycerin, propyleneglycol or other synthetic solvents; antibacterial agents, such as benzyl alcohol or methyl parabens; antioxidants, such as ascorbic acid or sodium bisulfate; chelating agents, such as EDTA; buffers, such as acetates, citrates or phosphates; and agents for the adjustment of tonicity, such as sodium chloride or dextrose. A parenteral preparation of the compositions of the disclosure can be enclosed in ampoules, disposable syringes or multiple dose vials made of glass or plastic, in accordance with standard practice in the field of the invention.

A number of devastating diseases including, for example, Cystic Fibrosis, Hurler's Syndrome, Duchenne and Becker muscular dystrophies involve the imposition of a premature stop codon rendering an otherwise functional gene inoperable. It is also been reported that the presence of premature stop codons in the IDUA and p53 genes may contribute to the development of various other disease states including perhaps some cancers. One strategy put forward to treating such diseases and disorders is to provide a compound which enables ribosomes to readthrough of inappropriately-placed stop codon. Various aspects as detailed below address this need by providing a congener of gentamicin and/or derivatives thereof that promote premature stop codon readthrough while exhibiting substantially less nephrotoxicity than gentamicin and most other aminoglycosides.

Gentamicin is an antibiotic complex produced by fermentation of *Micromonospora purpurea* or *M. echinospora* and variants thereof as described, for example, by U.S. Pat. Nos. 3,091,572 and 3,136,704, each of which are incorporated, herein by reference in its entirety.

Analysis has shown that the gentamicin complex is composed of at least four closely related, isomeric pseudo-oligosaccharides, each having a characteristic structure in which 2-deoxystreptamine is linked to two saccharide units, namely, garosamine and purpurosamine. See International Publication No. WO 2004/105688 A2. These four major gentamicin components differ from one another only in the nature of the methylation of the amine group at the 6' carbon of the purpurosamine unit licked to the 2-deoxystreptamine at the C-4 position, as can be seen in the following structural formula:

FORMULA 1

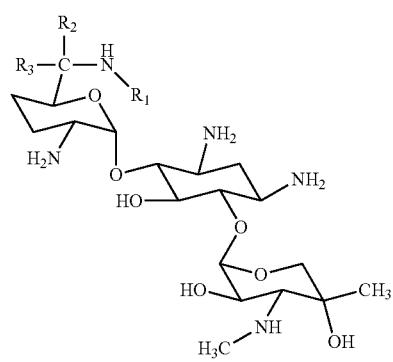

Gentamicin:
 $C_1$: $R_1=R_2=CH_3$; $R_3=H$
 $C_{1a}$: $R_1=R_2=R_3=H$
 $C_2$: $R_1=R_3=H$; $R_2=CH_3$
 $C_{2a}$: $R_1=R_2=H$; $R_3=CH3$ Clinically significant nephrotoxicity is characterized by elevated serum creatinine levels and a reduced Glomerular Filtration Rate (GFR). Accordingly, it is relatively easy to access the damage done the renal system by various nephrotoxins including, for example, many aminoglycosides. Numerous strategies have been developed to minimize the nephrotoxicity that is associated with aminoglycoside antibiotics. Approaches to limiting the toxicity of these compounds have included the introduction of an agent that alters uptake of the drugs or the intracellular trafficking of aminoglycosides. In this regard, high levels of dietary calcium or the use of polyaspartic acid has shown beneficial effects in animal models for nephrotoxicity. Another approach has been purification of nontoxic native components from mixtures of aminoglycosides, or the chemical modification of toxic aminoglycosides to produce less toxic substances. This approach has yielded two commercially available aminoglycosides that exhibit somewhat less nephrotoxicity than many commonly used aminoglycosides. Although certain aminoglycoside antibiotics are less nephrotoxic than others, most still exhibit an unacceptably high level of nephrotoxicity, and these compounds are especially ill suited for treating patients at high-risk for kidney problems.

Early clinical observations indicated that the nephrotoxicity of different gentamicin manufacturing lots were different. This led Kohlepp et al. to initiate studies to try and determine the relative toxicity of the various gentamicin components in animals. For an additional discussion of Kohlepp's work see, for example, Kohlepp S J, Loveless M O, Kohnen P W, Houghton D C, Bennett W M, Gilbert D N: *Nephrotoxicity of the constituents of the gentamicin complex, J. Infect. Dis.* 149: 605-614, 1984 (Kohlepp, et al.). Kohlepp, et al, were unable to clearly separate gentamicin into its various components. Therefore, Kohlepp et al.'s studies were carried on mixtures of gentamicin congeners which may have been enriched in a given congener of gentamicin C1, C1a, or C2 but this study was not carried out using isolated and purified congeners of gentamicin. Recently, we have isolated a forth congener from native gentamicin not identified in the Kohlepp et al., study cytotoxic. We refer to this as the C2a congener (Formula 1, FIG. 1). Because, Kohlepp et at were unaware of the presence of the C2a congener it must have been included in at least one of the fractions that that they did partially purify.

Accordingly, the result reported by Kohlepp et at may have miss-judged the toxicity of the partially purified fractions that they reported. For additional discussion of at least one method that can be used to purify and isolate components of gentamicin the reader is directed to, Sandoval R. M, Reilly J. P., Running, W, Campos, S. B., Santos, J. R., Phillips, C. L. and Molitoris, B. A., *A Non-Nephrotoxic Gentamicin Congener That Retains Antimicrobial Efficacy, J. Am. Soc. Nephrol.* 17: 2697-2705, 2006 (Sandoval et al.).

Results provided in Sandoval, et al., clearly identified the C2 congener of gentamicin as nontoxic in cell culture; the consistency between cell lines and the in vivo rat data confirm the nontoxic nature of the C2 component of gentamicin. In this study, the non-nephrotoxic C2 congener was found to be as potent a bactericide against Gram-positive and multi-drug-resistant Gram-negative bacteria as native gentamicin or any of the other congeners that were tested. Given its antibacterial activity and low cytotoxicity, the C2 congener could prove useful in the treatment of infectious diseases.

Many aminoglycoside antibiotics, while of major clinical importance in the treatment of serious gram negative infections and a potential therapeutic in the amelioration of symptoms caused by premature codon stop mutations, are associated with a high incidence of acute renal failure (ARF). More aggressive and broader therapeutic regimens using this less toxic compound can be used with patients who previously were deemed unsuitable for treatment with gentamicin because of their kidney disease or preexisting risk factors for developing kidney disease. Moreover, understanding the mechanisms of gentamicin's renal toxicity may provide insights leading to the development of co-therapies that use gentamicin.

While not wishing to be confined to a particular theory, the present inventors hypothesize that aminoglycosides, once internalized, are distributed throughout the proximal tubule cell to subcellular organelles via retrograde endocytic trafficking. Moreover, following this distribution, they induce organelle-specific injury, including alterations in intracellular vesicular trafficking and recycling of surface membrane components. The present inventors further believe, based on the data set forth below, that the cellular toxicity of the different components of gentamicin relates directly to their different intracellular trafficking.

The methods for treating pathologies caused by the insertion via mutation of premature stop codons into genes using the gentamicin components described herein may be applied to any animal, including humans, monkeys, equines, bovines, canines, felines, bovines, porcines and the like.

Isolation and Purification of the C2 Congener from Gentamicin (C2 Formula 1)

Referring now to Formula 1 and FIG. 1, 4 congeners can be isolated and purified from native gentamicin. Methods for isolating and purifying congeners include the following method. Briefly, separation of native gentamicin was carried out using a C18 column (250×4.60 mm) and the chromatograms was developed using a Waters 600e HPLC pump (Milford, Mass.). A gradient of 100% of a 0.1% (vol/vol) mixture of tri-fluoro-acetic acid in acetonitrile was used to develop the chronogram. Retention times of 12.87, 22.07, 23.84, and 25.85 minutes wee noted for congeners C1, C2, C2a, and C1a, respectively. There was no overlap between adjacent peaks. For all studies, the same lot of gentamicin was used. This ensured that the results obtained were independent of potential alteration in the ratio of gentamicin components. The purified C2 congener of gentamicin exhibited minimal cytotoxicity in cell culture. The molecule also exhibited excellent bactericidal properties against both *Bacillus subtilus* and a multi-drug resistant form of *Klebsiella pneumoniae*. In animal studies the C2 congener failed to induce the functional and pathologic changes characteristic of gentamicin nephrotoxicity such as that seen with the native compound. For additional discussion of this methodology please see, for example, Sandoval, et al.

There is already emerging interest in using aminoglycosides to treat these monogenetic diseases wherein the disease is due to a premature stop codon in a key gene. A series of studies have shown or discussed the potential benefit of using gentamicin to treat diseases such as Cystic Fibrosis, Hurler's Syndrome, Duchenne and Becker muscular dystrophies. Additional data indicate that the presence of premature stop codons in the IDUA and p53 genes can be overcome by gentamicin or Amikacin, but not Tobramicin. Unfortunately, because of gentamicin's high nephrotoxicity native gentamicin is ill-suited for the treatment of chronic diseases. However, of its reduced nephrotoxicity, and unexpected therapeutic benefits the congener C2 (C2 in Formula 1) holds great promise as a therapeutic agent for the treatment of genetic diseases arising from premature stop mutation defects, where continuous daily doses to increase transcription of complete proteins may be possible.

One embodiment is a congener of gentamicin, specifically the C2 congener which can be isolated from native gentamicin, and which exhibits almost the same therapeutic activity as gentamicin and a substantially lower level of nephrotoxicity than gentamicin. One aspect of the present disclosure includes using the C2 congener which promotes ribosomal readthrough of premature stop codons in mutated genes to treat various monogenetic diseases. Various aspects of the present disclosure relate to isolating the C2 congener from gentamicin or synthesizing the C2 congener or derivatives of the C2 congener and/or forming and/or using pharmaceutically-accepted salts of any useful from of the C2 congener for the treatment of genetic disorders whose etiology includes the imposition of premature stop codons into physiologically important genes.

The unexpected result that the C2 congener of gentamicin exhibits both reduced cell toxicity and promotes readthrough of premature stop codons presents an opportunity to treat diseases caused by premature stop codons, including some chronic disease, that will require repeated treatments with the compound throughout the patient's lifetime. Various aspects of the disclosure are directed to the treatment of diseases such as muscular dystrophy, cystic fibrosis, Hurler's Syndrome, and even various cancers that involve the imposition of a premature stop codon in the open reading frame of an important gene by administering doses of the C2 congener derivatives and formulations thereof over the lifetime of the patient.

One embodiment includes administering the C2 congener to a human or animal patient in the dosage and frequency of dosage governed by the mode of administration and dosage considerations conventionally employed with the aminoglycosides antibiotics, with the exception that C2, C2 derivatives and pharmaceutical preparations thereof, are considerably less nephrotoxic than most other aminoglycosides antibiotics including, for example, gentamicin. Accordingly, C2 congener based therapeutics can be safely administered at higher doses and/or for longer periods of time than can gentamicin or most of the other aminoglycosides.

Compositions and/or formulation that include the C2 congener (C2 in Formula 1) or derivative and/or salts thereof according to various embodiments can be administered intramuscularly or intravenously, or otherwise, as dictated by medical and pharmacological practice related to their use to treat gene-based diseases. For example, the composition of various embodiments may be administered in at least one dose, providing from about 3 to about 6 mg of the active agent/kg of patient body weight/day. In still another embodiment the composition is administered in a dosage so as to deliver about 1 mg/kg to 1.5 mg/kg of the gentamicin component C2 three times a day. In still another embodiment even higher doses may be administered as required to treat a given disease or disorder.

EXAMPLES

Materials and Method

Evaluating Renal Injury

Morphologic evaluation of injury caused by gentamicin and its congeners was assessed by grading the extent of necrosis of the proximal convoluted tubules. Injury scores were assigned on the basis of the predominant pattern present. For indirect immunofluorescence, 100 μm-thick sections were cut on a vibratome and stained with the monoclonal anti-gentamicin antibody (Biodesign International, Saco, Me.) and a fluorescein-conjugated secondary antibody (Jackson Immunoresearch, West Grove, Pa.) and lightly counterstained with Alexa 647 phalloidin (Molecular Probes) to localize filamentous actin for visualization using confocal microscopy.

Indirect Immunofluorescence Localization in LLC-PK1 Cells

Because of the high degree of cell death that were reportedly seen in the previous cytotoxicity assays with the congeners of gentamicin LLC-PK1 cells were allowed to reach approximately 70% confluence before being incubated in medium that contained 1 mg/ml of either native gentamicin or the congeners. During this period of exposure to native gentamicin or the congeners, lysosomes were labeled by adding a 10,000 molecular weight rhodamine dextran to the culture medium (0.5 mg/ml; Molecular Probes). The cells then were fixed and stained for indirect immunofluorescence and visualized via confocal microscopy. Briefly, the Golgi complex was localized with a fluorescein-conjugated lectin from *Helix pornotia* at 5 μg/ml (EY Laboratories, San Mateo, Calif.) diluted in solution that contained the CY-5 conjugated secondary antibody that was used in the indirect immunolocalization of gentamicin. Visualization of nonlysosomal, cytosolic gentamicin was carried out as described previously, using a Tyramide Signal Amplification (Molecular Probes).

Microscopy

Histological sections were viewed with a Wide field Nikon microscope with an attached color CCD camera (Nikon, Melville, N.Y.). Fluorescence images were acquired using a Bio-Rad MRC 1024 confocal microscope (Bio-Rad, Hercules, Calif.) on a Nikon platform (The Fryer Co., Huntley, Ill.). Co-localization studies with Texas Red dextran, FITC-*Helix pontatia*, and gentamicin were conducted on a Zeiss 510 confocal microscope with images illuminated and acquired sequentially to eliminate bleed-over emissions from the different fluorescence emission spectra.

Statistical Analyses

Student's T tests were conducted on serum creatinine values between congener C2 and the native compound at the various injection days and on Jablonski score values between congener C2 and the native compound using Excel 2003 (Microsoft Corp., Redmond, Wash.). Differences in necrosis, apoptosis, and cell density among the various congeners on the human and porcine cell lines were determined using an ANOVA function with Systat 11 software (Systat Software, Point Richmond, Calif.). Statistical significance was achieved at $P \leq 0.05$. All reported values are mean±SEM.

Example 1

Enantiomer C2 Exhibits Reduced Toxicity in LLC-PK1 Cells

Figure 1B:
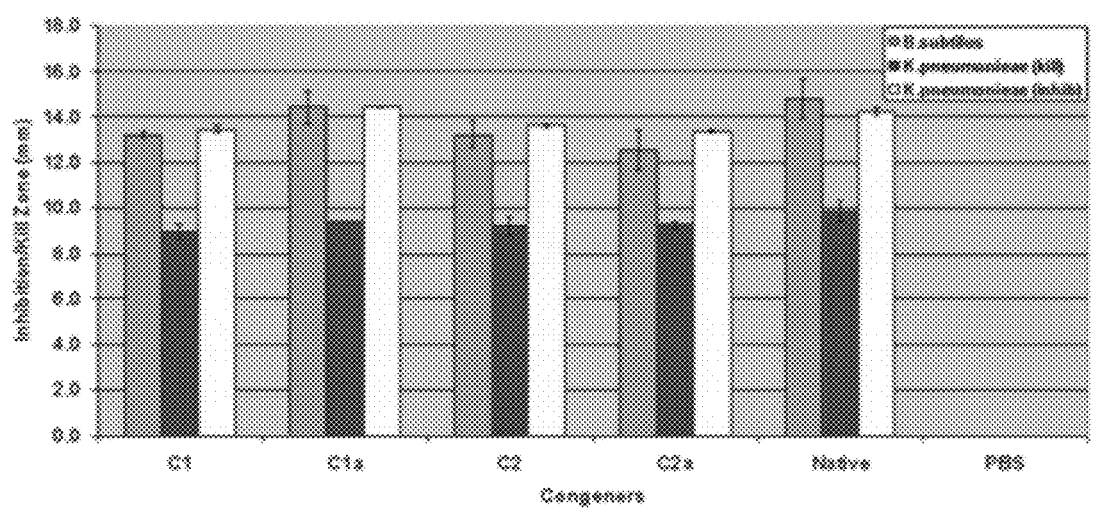

Because all the congeners were found to retain bactericidal activity, we next conducted cytotoxicity assays in culture using LLC-PK1 proximal tubule cells to determine the toxicity of each individual congener. Referring now to FIG. 1B. Cytotoxicity assays using cultured cells revealed that the first enantiomer separated, which we refer to as, for example, congener C2, the C2 congener of gentamicin or (C2 in Formula 1) exhibited markedly reduced toxicity even after 24 hours of continual exposure to the compound. Results in the porcine proximal tubule cell line LLC-PK1 were striking, Referring now to FIG. 2. (A) Apoptosis was assessed using the nuclear dye Hoechst 33342, which labeled nuclei of normal cells uniformly with a lower intensity and the nuclei of apoptotic cells more intensely and demonstrated the presence of condensed apoptotic bodies. The nuclear dye propidium iodide is cell impermeant and labels only necrotic cells, characterized by permeable cell membranes; co-localization of the two dyes gives a reddish-pink color. Surprisingly, all congeners except C2, showed evidence of widespread necrosis (A). For the congener C2, minimal evidence of toxicity was present. A histogram that was generated from the microscopic data revealed a toxicity index for C2 lower than any other individual component and lower than the native compound, $3.1 \pm 1.3$ and $8.9 \pm 3.4\%$, respectively (B). Cell density measured for cell populations exposed to the toxic C1, C1a, and C2a congeners dropped below 20% of control values. The values measured for cells exposed to C2 were significantly higher than any other congener and also higher than the native compound (*P~0.05) with reported values of $80.3 \pm 5.7$ and $58.5 \pm 7.7\%$, respectively. Values are means±SEM. Bar=approximately 10 microns.

Figure 2A:
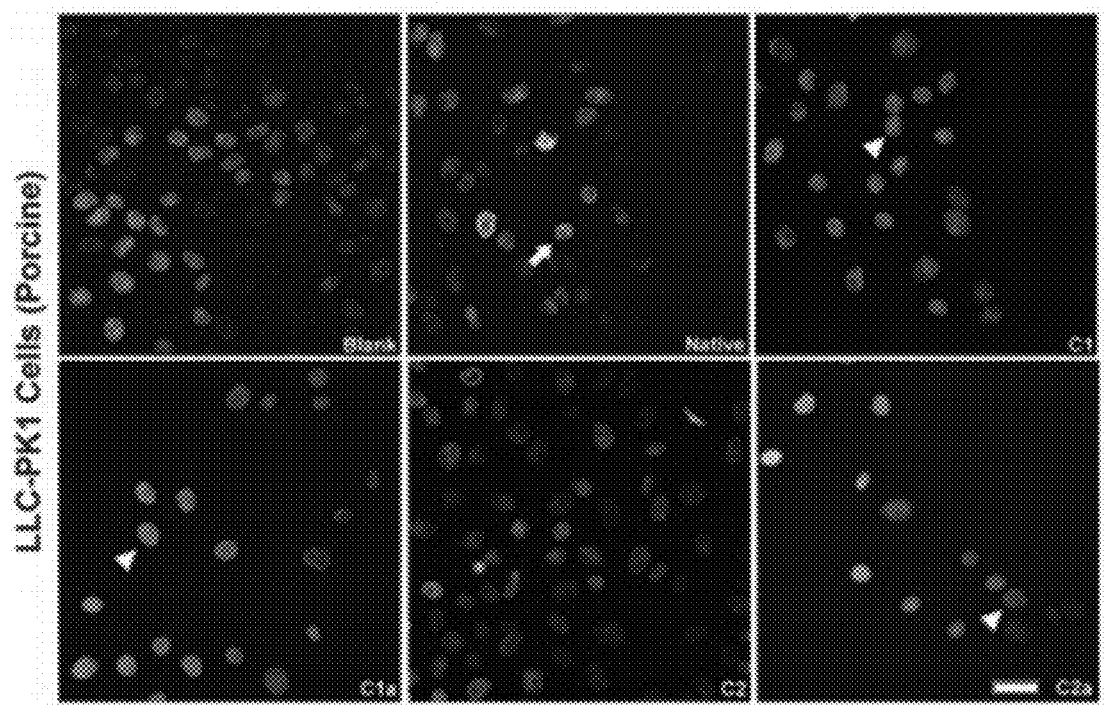
FIG. 2. Panel A, photomicrograph of porcine cells exposed to different compounds including native gentamicin various congeners isolated from native gentamicin and a buffer only control. Panel B, bar graph and line graph illustrating the relationship between cell density and exposure to cells exposed to a blank (not active compound) native gentamicin or various congeners isolated from gentamicin.
Figure 2B:
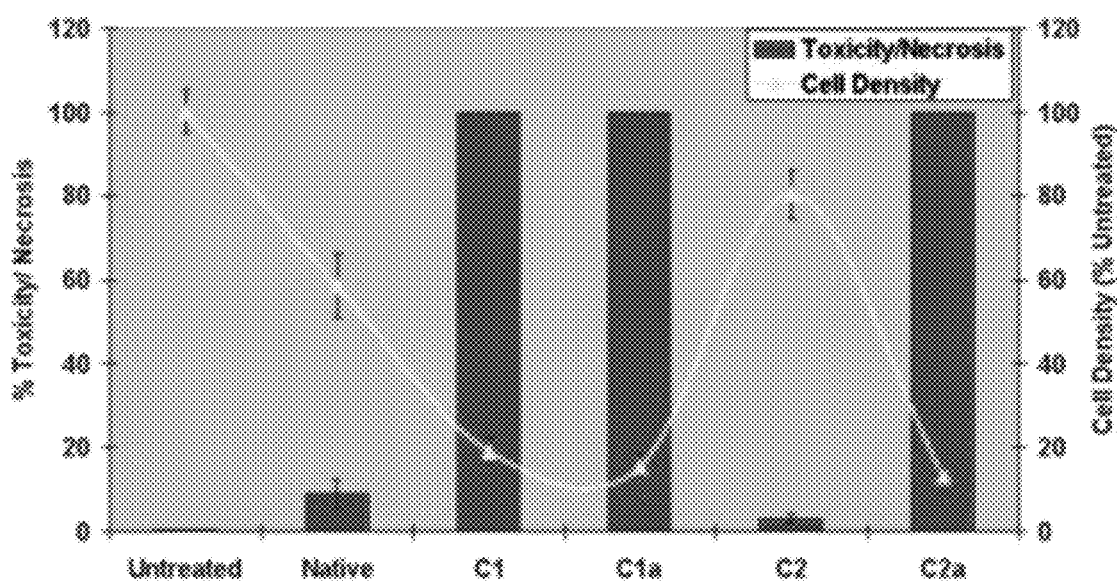
Figure 3A:
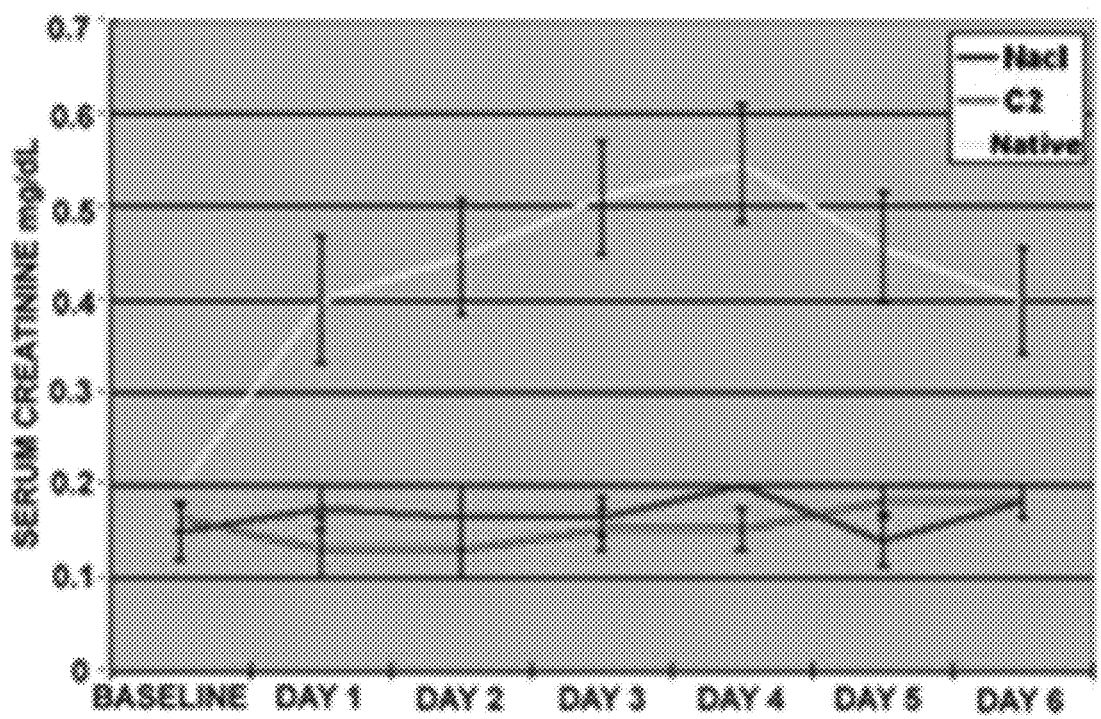
FIG. 3. Panel A, graph of serum creatine levels measured for Sprague-Dawley rats treated with either native gentamicin, or the C2 congener of gentamicin. Sections from each animal were stained with either data were collected over a seven day period. Panel B, C, D and E, photomicrographs of tissue samples collected from Sprague-Dawley rats treated with one of the following, native gentamicin, and the C2 congener of gentamicin. Sections were stained with either Hematoxylin and eosin (H&E) or periodic-acid Schiff (PAS. Panel F, bar graph showing the Jablonski score a measure of kidney damage for animals treated with the following compounds: a salt solution; native gentamicin, or the C2 congener of gentamicin. Panels G and H, photomicrographs of renal tissue collected from animals treated with either native gentamicin or the C2 congener of gentamicin.
Figure 3B:
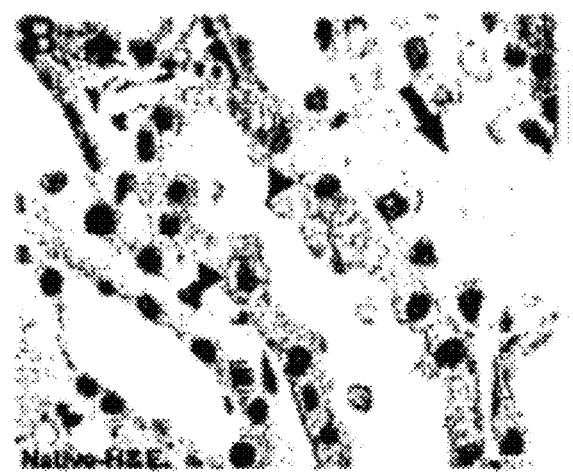
Figure 3C:
Figure 3D:
Figure 3E:
Figure 3F:
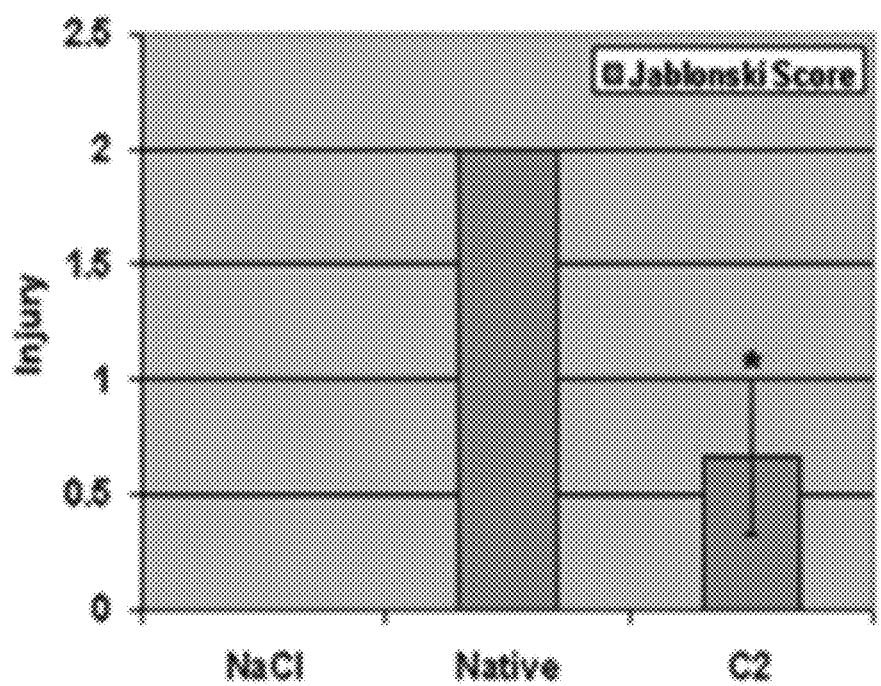
Figure 3G:
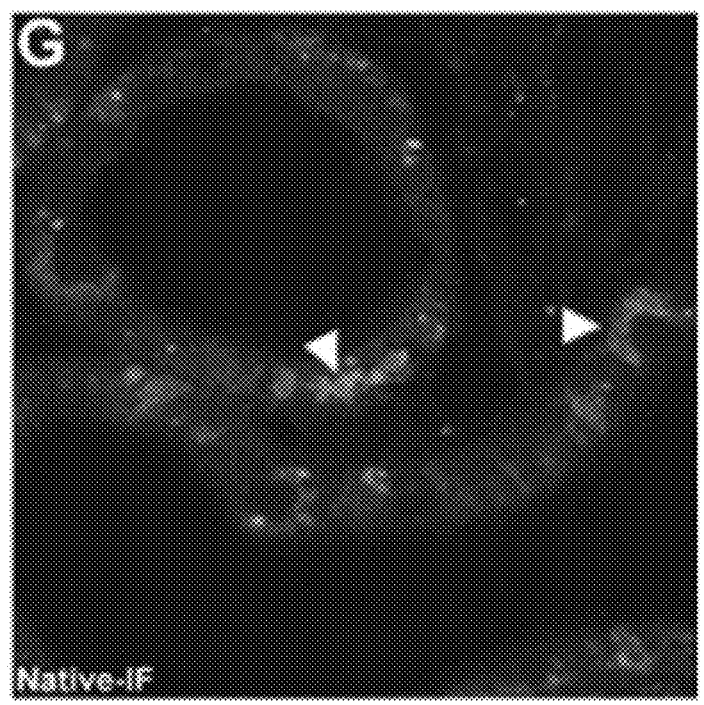
Figure 3H:
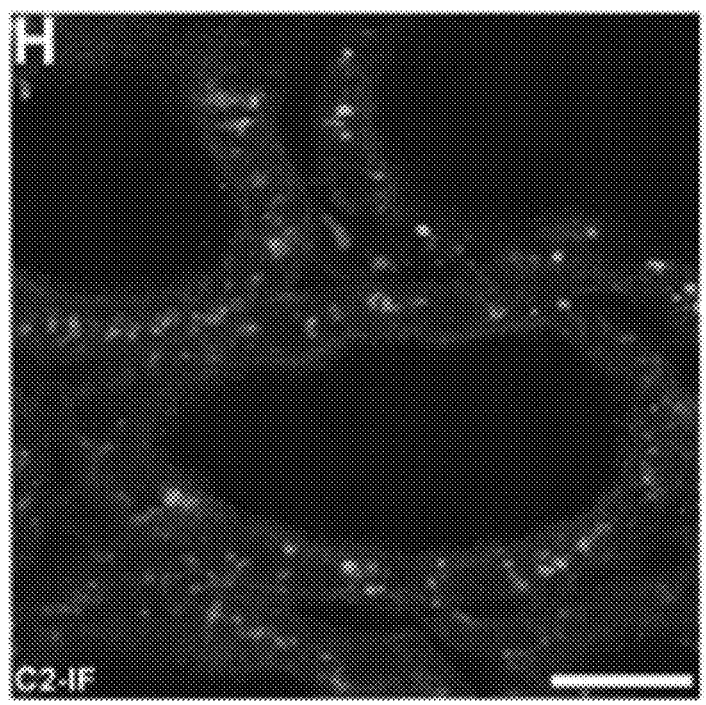
Figure 4A:
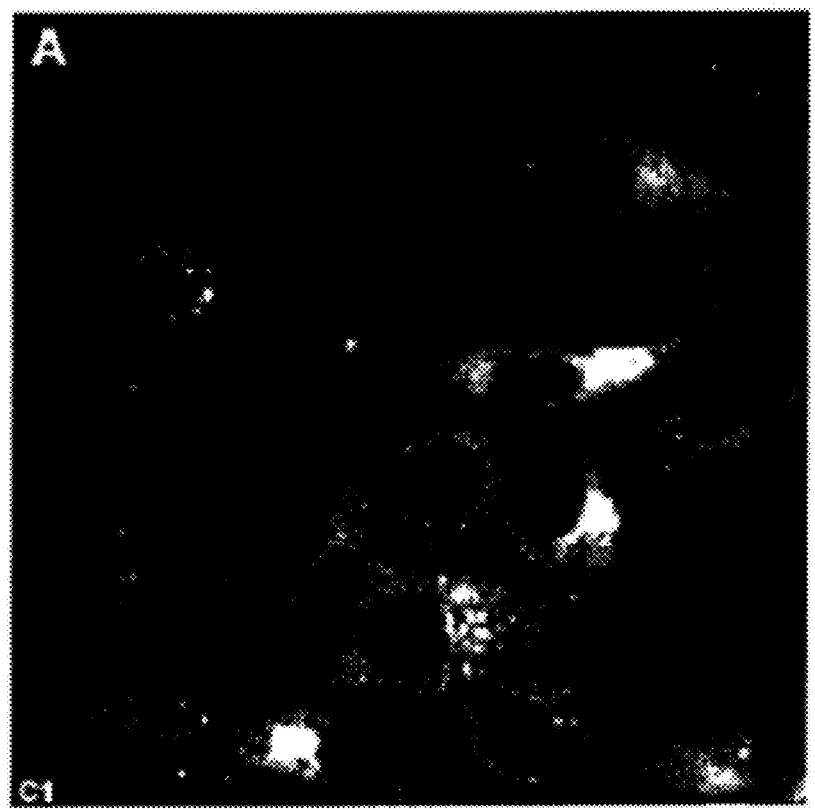
FIG. 4. A photomicrograph illustrating the effect on LLC-$PK_1$ cells of short-term exposure to native gentamicin, cells in panels A-D were treated with congeners C1, C1a, C2 and C2a, respectively.
Figure 4B:
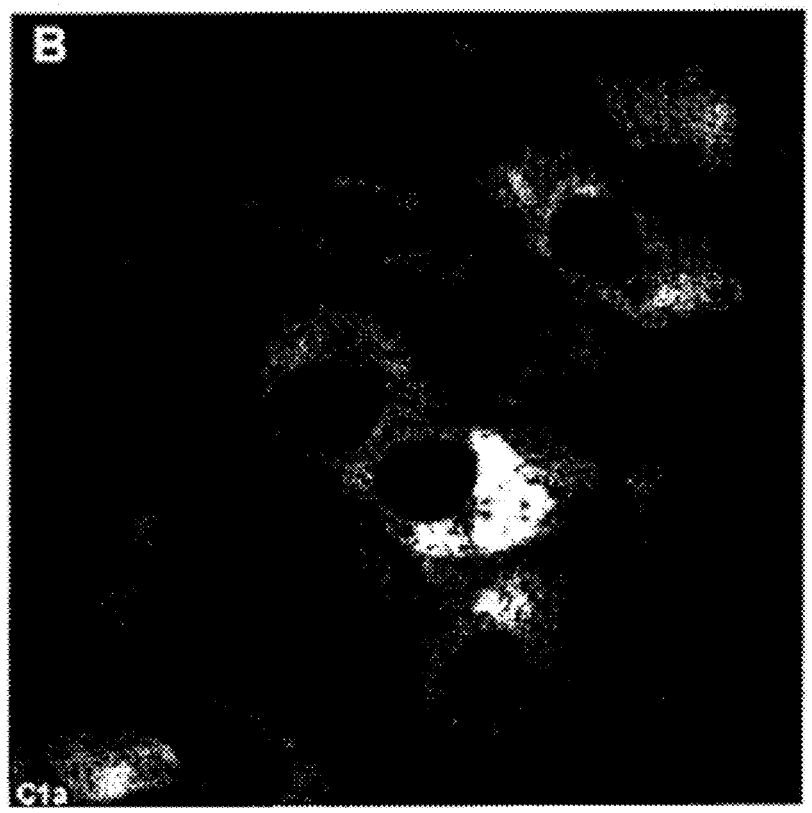
Figure 4C:
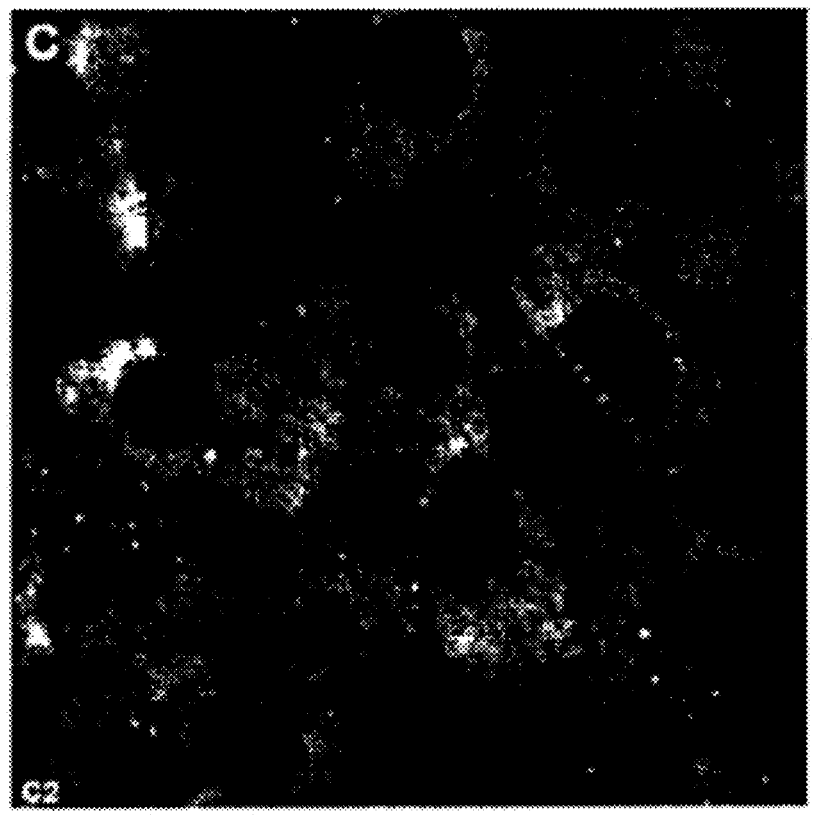
Figure 4D:
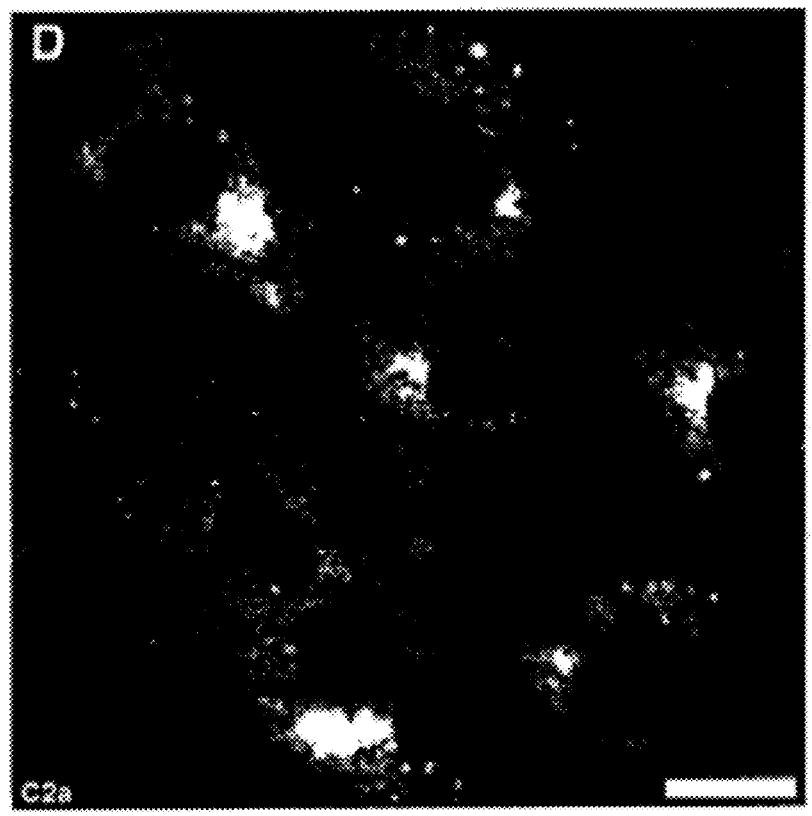

The nuclear dyes propidium iodide and Hoechst 33342 were used as markers for necrosis and apoptosis, respectively. In this assay, the cell permeate dye Hoechst 33342 labeled nuclei of all cells with an even distribution (FIG. 2A, Blank). Apoptotic cells were discerned from normal cells by condensation of nuclear material and increased localized fluorescence (FIG. 2A, native, arrow). Necrotic cells incorporated the cell-impermeant dye propidium iodide and displayed a pink color when combined with the cyan color of the Hoechst 33342 (FIG. 2A, C1, C1a, and C2a, arrowheads). Here, a marked difference in cytotoxicity among the various congeners was observed. All congeners except C2 had 100% toxicity at 24 hours of exposure (FIG. 2). Conversely, the percentage of cell death with the C2 congener was $3.1 \pm 1.3$ and $8.9 \pm 3.4\%$ for the native mixture. This combination of cell death and inhibition of cell growth resulted in cell density values that were significantly higher for the C2 congener than with the native compound, with values of $80.3 \pm 5.7$ and $58.5 \pm 7.7\%$ ($P \leq 0.05$) of untreated values, respectively. Both of these values were elevated when compared with values that were measured for the C1, C1a, and C2a, congeners all of which all were <20% of untreated values (FIG. 2 B). The data suggest that the C2 congener of gentamicin has minimal cytotoxicity and may actually reduce the toxicity of the other gentamicin congeners when it is present in mixtures such as native gentamicin that include other congeners.

Example 2

Six Days of Daily Exposure to Enantiomer C2 is not Nephrotoxic in Sprague-Dawley Rats Having identified a gentamicin congener with reduced toxicity in cultured cells, we next set out to determine the toxicity of this congener in vivo. Referring now to FIG. 3 A, male Sprague-Dawley rats that were given either the C2 congener at 100 mg/kg per day or normal saline intraperitoneally for six daily doses showed no elevation in serum creatinine. In these groups, serum creatinine values remained $\leq 0.2$ mg/dl up to 24 hours after the last injection. However, rats that were given the same dose of native gentamicin exhibited elevated serum creatinine levels 24 hours after the first injection. The serum creatinine values of the animals given gentamicne nearly tripled to a peak value of 0.55 mg/dl 24 hours after the fourth injection. We specifically used six daily doses for these studies to allow additional time for the C2 component to induce injury, because it is widely known that serum creatinine rises early in this model when native gentamicin is used. It appears that even after prolonged exposure to the C2 congener there was no change in serum creatinine values, and these values remained significantly lower than those of animals treated with native gentamicin ($P \leq 0.05$).

Example 3

Six Days of Daily Exposure to the C2 Congener Induces Few Alterations in Kidney Morphology or Histology Referring now to FIG. 3 B-H, a general histological survey of the rat kidney tissues was conducted to determine whether gross morphologic changes accompanied differences that were observed in renal function. Again, these studies were conducted after 7 days of exposure, or six doses of gentamicin. This was to ensure that we would see any delayed nephrotoxicity from the C2 congener. These studies occurred at a time when the native gentamicin-treated animals were recovering, as evidenced by a reduction in serum creatinine levels in these animals. Therefore, these studies likely underestimate the actual histological damage that occurred early on in animals treated with native gentamicin. Hematoxylin and eosin (H&E)-stained sections from rats given native gentamicin exhibited cell sloughing and debris in the tubular lumens (FIG. 3 B, arrows). In addition, large perinuclear vacuoles (FIG. 3 B, arrowheads) could be seen in the renal corticol area. Hematoxylin and eosin H&E-stained kidney sections of rats given native gentamicin compound showed extensive proximal tubule cell damage (FIG. 3 B). Here, proximal tubules from native gentamicin treated rats contained cast material and shed cells in the lumen (thick arrow). In addition, many of the proximal table cells contained large vacuoles that localized around the nucleus (FIG. 3 B, arrowheads).

Referring now to FIG. 3 C, in contrast, kidney sections from rats that were treated with the C2 congener of gentamicin and stained with (H&E) exhibited normal morphology. Sections from animals treated with the C2 congener exhibited few exfoliated epithelial cells in the tubular lumens, with intracellular vacuoles, when present, smaller and more evenly dispersed throughout the cytosol (FIG. 3 C, arrowheads). Tubular epithelial cells were cuboidal, and the lumens lacked cellular debris. Occasionally, vacuoles appeared within the tubular epithelia in proximal tubule cells from C2-treated rats, but they were generally much smaller in size, fewer in number, and not localized to the perinuclear area. Rats that were exposed to normal saline exhibited morphology similar to that seen with the C2 congener (data not shown).

Referring now to FIG. 3 D-E, thin histological sections also were stained with PAS to localize the glycocalyx that was associated with the brush border membrane of proximal tubules. Here, a violet color that is associated with the glycocalyx-rich microvilli helps delineate changes to the brush border. Referring now to FIG. 3O, in rats that were exposed to the native gentamicin compound, the proximal tubular brush border seemed to be reduced in size. As with the sections stained with H&E, these tubules contained intralumenal debris (FIG. 3 D, arrows) and intracellular vacuoles (arrowheads). Referring now to FIG. 3 E, the proximal tubular brush borders of rats that were exposed to congener C2 exhibited more abundant and enriched PAS staining, defining the taller apical membranes (FIG. 3 E, thin arrows), similar to that observed in saline-treated rats (data not shown).

Referring now to FIG. 3 F, results from a modified Jablonski score, determined to assess damage in the cortex, and showed that renal injury was significantly reduced in animals that were treated with the C2 congener as compared with animals that were treated with native gentamicin (P_0.05). A tissue sample from an animal in the control (dosed with only a salt solution) exhibited not evidence of injury.

Referring now to FIG. 3 G-H, when tissues from rats that were exposed to the native commercial gentamicin compound or the C2 congener of gentamicin were processed for indirect immunofluorescence localization of gentamicin, a difference in the intracellular accumulation and distribution emerged. The formation of myeloid bodies or cytosegresomes within proximal tubule cells has been a hallmark alteration associated with prolonged exposure to aminoglycosides. Here, formation of these structures in rats that were exposed to the native gentamicin compound was seen (FIG. 3 G, arrowheads). In these tissues, the lysosomes appeared swollen and greatly reduced in number, and they often were localized around the nucleus. In contrast, rats that were exposed to congener C2 exhibited what would be deemed normal lysosomal morphology (FIG. 3 H). In these tissue sections, lysosomes seemed much more numerous, smaller in diameter, and diffusely distributed throughout the cytosol. They were not segregated around the nucleus as noted in section from animals treated with the native compound. Tissue sections from rats that were treated with normal saline alone and processed identically for immunofluorescence localization produced no fluorescence associated with gentamicin localization (data not shown).

In summary, referring now to FIG. 3 D, exposure to the native compound resulted in a reduced apical brush border staining the thin arrows point to areas that clearly show a reduction in the purple color along the brush border of these heavily vacuolized cells (arrowheads). Debris within the tubular lumen again was seen in rats given the native compound (thick arrow). Rats exposed to the C2 congener exhibited brighter PAS staining (FIG. 3 E, thin arrows), indicative of a better maintained or normal apical brush border. Again, fewer large intracellular vacuoles, and less cellular debris, were seen in the tubular lumens. H&E-stained sections were scored using a modified Jablonski score with results shown in FIG. 3F. The reduced cellular injury that was seen in C2-treated rats was significantly lower than that seen in native gentamicin-treated rats. Localization of the C2 congener or native gentamicin via indirect immunofluorescence revealed different localization patterns. Renal tissue of animals treated with native gentamicin exhibited large aggregates around the nuclei of proximal tubule cells (FIG. 3C, arrowheads), with a few large punctuate aggregates. Renal tissue of animals treated with the congener C2 showed localized, smaller, discrete punctuate structures dispersed throughout the cytosol, forming fewer perinuclear aggregates (FIG. 3G-H). Bar=approximately 20 microns.

Example 4

Short-Term Exposure to the Individual Congeners Reveals No Difference in Early Nonlysosomal Trafficking Previous studies from two laboratories have documented the importance of cytosolic release of aminoglycosides in subsequent LLC-PK1 cell injury. For additional discussion on this topic see, for example, Servals H, Van Der Smissen P, Thirion G, Van der Essen G, Van Bambeke F, Tulkens P M, Mingeot-Leclercq M P: *Gentamicin-induced apoptosis in LLC-PK1 cells: Involvement of lysosomes and mitochondria.* Toxicol Appl Pharmacol 206: 321-333, 2005. Therefore, we hypothesized the non-nephrotoxic C2 component of gentamicin might not be released as rapidly or to the same extent as the other toxic gentamicin components. To test this hypothesis directly, we used our previously reported endosomal/lysosomal quenching and Tyramide amplification techniques to evaluate the early phase of cytosolic gentamicin trafficking.

Referring now to FIG. 4, a photomicrograph illustrating the effect on LLC-PK$_1$ cells of short-term exposure to native gentamicin. FIG. 4 panels A, B, C and D show sections from animals treated with C1, C1a, C2 and C2a, respectively. The individual cytotoxic congeners of gentamicin or the less toxic C2 congener of gentamicin revealed no difference in early, nonlysosomal trafficking. Cells were exposed to the various congeners of gentamicin (1 mg/ml) for 1 hour and processed for lysosomal quenching, and Tyramide Signal Amplification of gentamicin. Uniform trafficking to the endoplasmic reticulum (ER) was observed with for all of the congeners tested. Cytosolic release was not yet detected at this early time point as is evident by the lack of localization within the nucleus. Bar=approximately 10 microns. A, C1; B, C1a; C, C2; D, C2a.

The results shown in FIG. 4 indicate that we could discern no difference in the extent of cytosolic release 1 h after exposure to any component of gentamicin. In all cells, for all congeners, there was rapid appearance of a homogeneous cytosolic distribution of gentamicin. Therefore, all of the congeners isolated from native gentamicin that we tested reached the cytosol rapidly. Accordingly, these data do not explain the differences that were noted in cell injury among the various components.

Example 5

Figure 5:
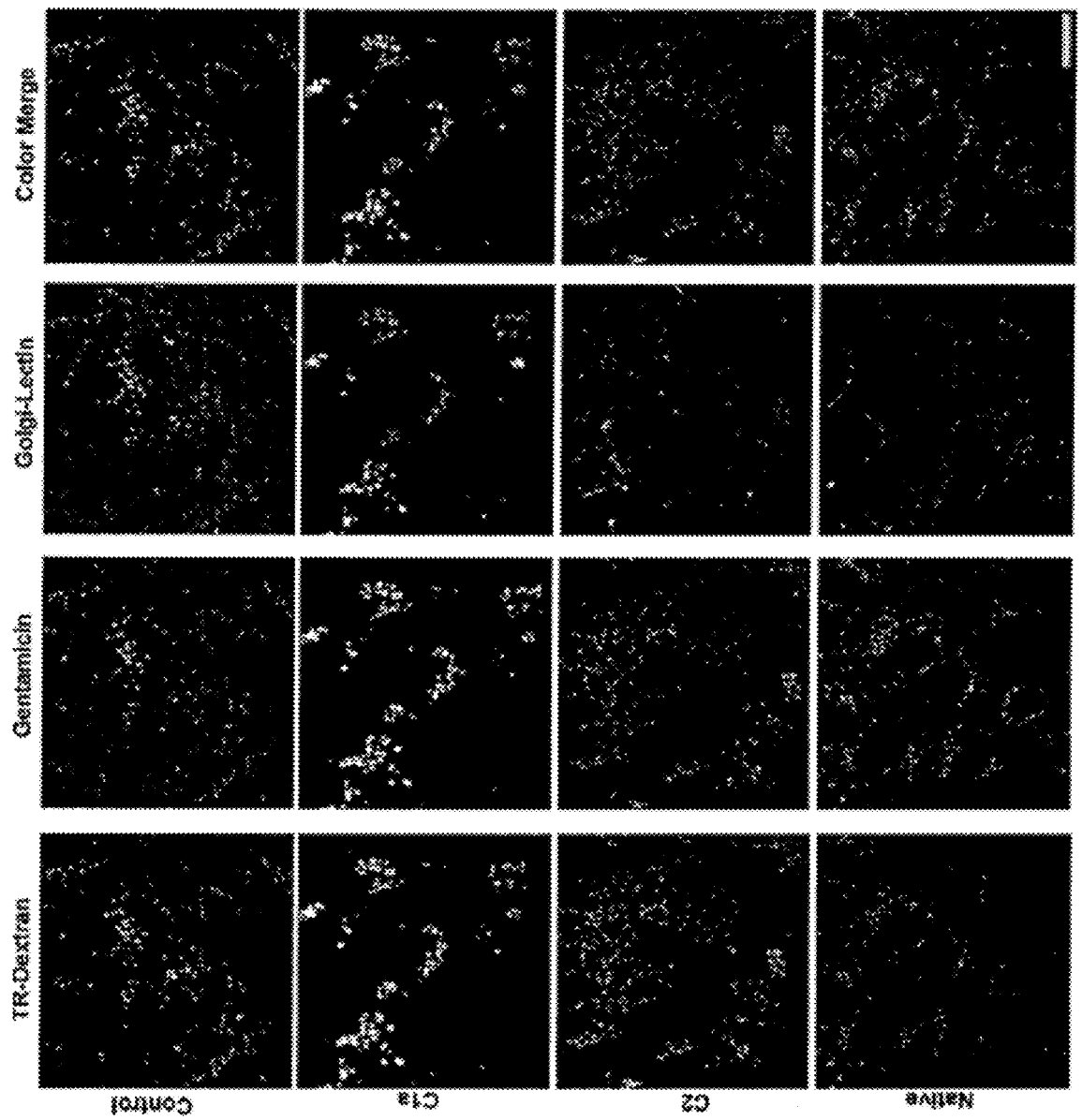
FIG. 5. Photomicrographs illustrating the effect on LLC-PK1 cells of long-term exposure to cytotoxic congeners; induced coalescence of lysosomes and the Golgi complex. Cells were treated as indicated by the row assignments with one of the following compounds: control (no test compound), the C1a congener; the C2 congener or native gentamicin. Cells so treated we then visualized for the presence of TX-Red (which stains the lysosomes); introduced gentamicin; or Golgi-Lectin, columns 1-3, respectively. The images in column 4 labeled color merge show composite images of the images in each row in the preceding columns 1-3.

Large Perinuclear Accumulations of Cytotoxic Gentamicin Congeners Contain. Elements Of Both Lysosomes and the Golgi Complex In order to study long-term differences in the intracellular distribution of gentamicin, we undertook additional study of gentamicin distribution in LLC-PK$_1$ cells. Referring now to FIG. 5. After 24 h of continuous exposure to the native gentamicin mixture, congener C2, or the cytotoxic congeners and a 10,000 molecular weight Texas Red dextran to localize the lysosomes, cells were fixed and processed for the localization of the Golgi complex with a FITC-conjugated lectin from *Helix poniatia* and indirect immunofluorescence localization of gentamicin with a Cy-5-conjugated secondary antibody. The staining patterns that were observed for the native compound, congener C2 and congener C1a (as a representative of the altered morphology seen with all cytotoxic congeners) are shown in FIG. 5.

Still referring to FIG. 5, photomicrographs illustrating the effect on LLC-PK1 cells of long-term exposure to cytotoxic congeners; induced coalescence of lysosomes and the Golgi complex. Texas Red dextran (0.5 mg/ml) was present in the media during gentamicin exposure to label the lysosomes. In untreated cells and cells treated with the C2 congener, the lysosomes appear as small, discrete vesicles found throughout the cellular cytosol. Cells exposed to native gentamicin exhibited some perinuclear accumulation of gentamicin and Texas Red dextran, although both were still largely were confined within smaller vesicles. Cells exposed to the cytotoxic congeners, as shown here with C1a, produced much larger swollen vesicles that encompassed the nucleus. When gentamicin was introduced into the cells and visualized, the compound co-localized with the lysosomes. Visualization of the ER-Golgi-intermediate-compartment/cis-Golgi complex with a lectin from *Helix pomatia* was faint in untreated cells, congener C2-treated cells, and the native gentamicin-treated cells. Movement of the lectin epitope during normal cellular trafficking may account for the faint staining that was seen at this concentration. Cells exposed to congener C1a exhibited intense staining of *Helix pomatia*, producing a pattern that was identical to that seen with the Texas Red dextran and gentamicin. Bar=approximately 10 microns.

Exposure to gentamicin, as either the native mixture or the individual congeners, showed co-localization between the dextrans and gentamicin in lysosomes, as expected. In untreated cells or cells that received congener C2, lysosomes seemed numerous, small, and evenly distributed throughout the cytosol, as previously noted in the rat studies. In contrast, the lysosomes in cells that were exposed to cytotoxic congeners or the native gentamicin mixture were located in a perinuclear position and swollen, as seen here with the C1a congener. The Golgi complex in cells that were treated with the C2 congener, but not those that were exposed to the cytotoxic congeners was faint. Some staining in these cells also occurred in the periphery of the cell, likely as a result of the recognition of carbohydrate moieties located at the surface of the cells. Cells that were exposed to the cytotoxic congeners produced a Golgi staining pattern that was identical to that of lysosomes and gentamicin as seen with cells exposed to the C1a congener.

Still referring to FIG. 5, the intensity of the lectin staining was markedly increased with little or no staining within the remaining cytosol or the cell surface. In a staining pattern that was reminiscent of immunolocalized native gentamicin in rats, cells that were treated with C1a exhibited large grape-like clusters around the nucleus and contained gentamicin and both lysosomal and Golgi complex markers. Cells that were exposed to the C2 congener lacked these structures, and there was no overlap between the lysosomal and Golgi complex markers. The staining pattern for the native compound was more heterogeneous, with accumulation patterns in between those seen for either C2 or C1a.

Without wishing to be bound by any specific hypothesis, theory or explanation and presented by way of explanation and not limitation these unexpected results suggest that the cytotoxic gentamicin congeners induce a trafficking abnormality after prolonged exposure to the compounds. Treatment with the native gentamicin mixture exhibited effects on trafficking that were in between the two extremes seen with cells exposed to either the non-toxic C2 congener or the very toxic C1a congener of gentamicin. These results presented in FIG. 5, also suggest indicate that inclusion of the C2 component may reduce the intracellular trafficking abnormality that is induced by the nephro-toxic congeners.

Example 6

Proposed Mechanism for Variations in Gentamicin Congener Nephrotoxicity

Cytosolic release, a pathway for gentamicin trafficking that was identified previously in our laboratory and confirmed recently by Servais et al. is a characteristic shared by all of the gentamicin congeners (Formula 1, FIG. 1 A) tested in this study, including the non-nephrotoxic C2. Referring now to FIG. 5. Although this potential explanation for the lack of toxicity that was seen with C2 was eliminated as disclosed herein, we did observe a deleterious alteration to the Golgi complex and lysosomes, characterized by coalescing of the two into a large amorphous compartment. These structures, presumed to be "myeloid bodies" that classically have been associated with gentamicin toxicity, were produced by the cytotoxic congeners, but not by the non-nephrotoxic C2 congener. This alteration was apparent in cultured cells after 24 hours of continuous exposure and in proximal tubule epithelial cells in rats that were subjected to daily exposure for 6 days. This effect is similar to the trafficking effects that were induced by Brefeldin A, another fungal metabolite, in certain cell lines.

Cells that were exposed to the congener C2, stained only faintly with *Helix pomatia*, a lectin that is known to label the cis-Golgi and endoplasmic reticulum-Golgi intermediate compartments. Hence, shuttling of the lectin epitope between the endoplasmic reticulum and Golgi complex could account for the reduced intensity at the concentration used in the study. In contrast, the intensity that was seen at the Golgi complex when the cytotoxic congeners were used (represented by C1a in FIG. 5) was very intense and localized in grape-like clusters around the nucleus. This may arise from an accumulation of Golgi elements in a stagnant organelle. These alterations occurred within the entire lysosomal pool and not just within newer endosomal bodies that formed after gentamicin exposure, because preincubation with dextrans to label lysosomes, followed by a chase and subsequent gentamicin exposure for 24 hours, produced identical results (data not shown). Similar structures also were seen in our previous studies and allowed for easy identification of the Golgi complex. The affects on this pathway were much more severe when cultured cells were exposed to the individual cytotoxic congeners as compared with the native compound. This observation again strongly suggests that the inclusion of the C2 congener, in the native mixture, affords protection against the effects of the cytotoxic congeners. Therefore, on the basis of the data presented here, the naturally occurring variation in the percentage of C2 congener composition of native gentamicin from commercial lot to lot could account for the previous clinical observations regarding variable nephrotoxicity.

Example 7

Eight mdx mice are treated with I.M. injections of either gentamicin or the C2 congener of gentamicin (C2 in Formula 1) four of the mice receive either gentamicin or the C2 congener at a dose of about 1 mg/day and the other four mice receive the same compounds at a dose of about 5 mg/day. The animals are dosed over a period of 7 days. As controls, some normal mice and some mdx mice do not receive any gentamicin or C2 but are other wise treated the same as all of the other animals in the study. All mice are sacrificed, their skeletal muscle and their hearts are frozen and cryostat sectioned. The presence of dystrophin in these sections is investigated by immunohistochemistry. Strong dystrophin immunostaining is observed in the normal skeletal and heart muscles. In the untreated mdx muscles, dystrophin immunostaining is observed only in a few reverent fibers. Dystrophin is detected by immunohistochemistry on all muscle fibers and all heart muscle cells of the mdx mice that are treated with gentamicin or C2. In some muscles of mice that are treated with 5 mg/day of gentamicin the staining appears as intense as that observed in the normal mouse muscles. The dystrophin staining is less intense in the muscles of mice treated with 1 mg/kg. Therefore a dose of about 8 to 40 mg per Kg of body weight per day of either gentamicin or the C2 congener of gentamicin successfully suppresses the premature stop codon by inserting an amino acid, and continuing translation of gentamicin-encoding nucleic acids. Subcutaneous and intravenous administration will provide the same results. The duration of the course of treatment may vary. For the purpose of the present demonstration, the i.m. treatment lasts for 7 days. Sub-cutaneous or intra-muscular daily treatments of 7 to 14 days or longer should also thought to be equivalently successful, given the low nephrotoxicity of the C2 congener it an its derivatives are the preferred for long term treatment of gene based diseases which may require lifetime dosing with the compounds.

Example 8

Assessing the Effects of Gentamicin and Specific Congeners of Gentamicin on Cytotoxicity Gentamicin and various congeners isolated and purified by, for example, the HPLC techniques outlined in Sandoval et al. were tested to assess their level of cytotoxicity. Briefly, COS7 cells were grown in the presence of either 200 or 500 ug/ml of one of the following test compounds, the C1 or the C2 congeners of gentamicin or native gentamicin. As a control still another batch of COS7 cells were grown in absence of all of the test compounds.

Figure 6:
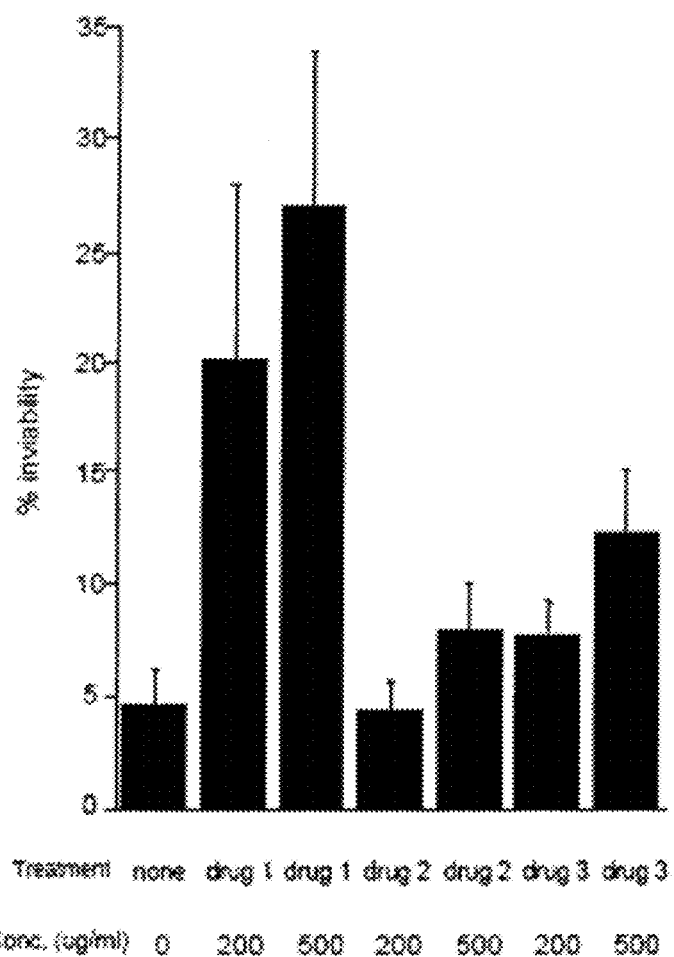
FIG. 6. A graph illustrating the effect on cell death (inviability) measured for: a control (no gentamicin or congener of gentamicin); the C2 congener of gentamicin, labeled as Drug 1, present at either the 200 ug/ml level or 500 ug/ml level; the C2 congener of gentamicin, labeled as Drug 2, present at either the 200 ug/ml level or 500 ug/ml level; or native gentamicin, labeled as Drug 3, present at either the 200 ug/ml level or 500 ug/ml level.

Referring now to FIG. 6 cell inviability was determined for cells exposed to no test compound, native gentamicin or a congener of gentamicin; in this graph a high value indicate low cell toxicity. Cell death (% inviability) was determined for each of the six conditions. The C1 congener, labeled Drug 1 in FIG. 6, exhibited the greatest toxicity, followed by native gentamicin, and labeled Drug 3 in FIG. 6. In contrast, the C2 congener, labeled Drug 2 in FIG. 6, exhibited virtually no toxicity, comparable to the control, when it was administered to the cells at the 200 ug/ml level and only very minimal toxicity when it was administered to the cells at the 500 ug/ml level.

Example 9

Assessing the Effects of Gentamicin and Specific Congeners of Gentamicin on Stop Code Readthrough Native gentamicin and various congeners prepared by the methods described in the above were tested to determine their effect of stop codon readthrough. Briefly, the percentage of readthrough of the stop codon UGAC was measured after exposure to one of the following compounds: congener C1, or C2 of gentamicin or native gentamicin. The method used to assess readthrough is as follows.

A plasmid including hCFTR-G542X under control of the rat FABP promoter was derived from a FABP-hCFTR-WT plasmid. The G542X premature stop mutation was introduced by the direct exchange of a 3043 by BspEl/NcoI fragment from pDB436, yielding the FABP-CFTR-G542X plasmid pDB488. In addition to the G542X mutation, this plasmid contains an additional SalI restriction site that was introduced at codon 764 of the CFTR cDNA. This new restriction site does not alter the amino acid sequence of the CFTR protein.

In order to determine the optimal concentrations of the aminoglycosides to use in the mammalian translation system, increasing amounts of each aminoglycoside were added to a rabbit reticulocyte translation system while expressing the QX(N) (UGAC) construct. The effect of aminoglycoside addition on total protein synthesis was monitored by comparing the total amount of proteins synthesized in the presence and absence of various aminoglycosides. A range of aminoglycoside concentrations was then determined that allowed a maximal amount of termination suppression without inhibiting total protein synthesis more than two- to threefold. In vitro translation reactions were carried out using the TNT coupled transcription/translation system (Promega). Each reaction was carried out in a total volume of 12.625 µl and contained: 6.25 µl reticulocyte lysate, 0.625 µl 20×TNT reaction buffer, 2.5 µl 20 mM rNTPs, 0.25 µl 1 mM amino acids (minus methionine), 1.0 µl [35S]methionine (11 µCi/µl; NEN-Dupont), 0.25-µl 40 U/µl RNAsin inhibitor (Promega), 0.25-µl 80 U/µl SP6 RNA polymerase (Promega), 1.0 µl 1 mg/ml DNA template, 0.5 µl H2O, tobramycin, amikacin (Calbiochem), or gentamicin (Gibco). The mixture was incubated for 2 h at 30° C., 12.6 µl of sodium dodecyl sulfate sample buffer was added to each reaction, and the samples were boiled. Then 1-2 µl of each sample was loaded onto a 12.5% sodium dodecyl sulfate polyacrylamide gel. The gel was dried and subjected to PhosphorImager analysis in order to quantitate the amount of truncated and full-length protein species. The percentage of readthrough was then calculated as the amount of full-length protein/(truncated+full-length species)×100.

Foci assays were carried out as follows. Rat embryo fibroblast (REF) cells were obtained from American Type Culture Collection (#CRL-1764) and cultured in Dulbecco's modified Eagle's medium supplemented with 10% fetal calf serum at 37° C. with 5% CO2. An H-ras construct containing the dominant-negative mutation G12V was provided by Dr. Michael Cole, Princeton University. A 6.6-kb BamHI fragment containing the H-ras cDNA was subcloned into pcDNA3.1 Zeo (Invitrogen) under cytomegalovirus promoter control. The murine genomic P53 construct, long terminal repeat (LTR)—P53val, contained an A135V mutation and was expressed under LTR promoter control. This construct was generously provided by Dr. Michael Ruppert, University of Alabama at Birmingham. The R210X mutation was introduced into LTR-P53val by site-directed mutagenesis. The REF cells were transfected at 60-70% confluency in a six well (35 mm2 per well) culture dish with the indicated plasmids using 2 µg total DNA and 8 µl lipofectamine (Gibco-BRL) for 4 h in the presence of sera. Aminoglycosides were added 24 h after the transfection. For these experiments 200 ug/ml of either toxic Congener C1a (Drug 1, in graph), Non-toxic Congener C2 (Drug 2), or native gentamicin (Drug 3) were added. Foci began to form approximately 2-3 days after the REF cells reached confluency and the number of foci in each 35 mm2 well was determined in a blinded manner. A lacZ gene was subcloned into the pcDNA3.1 Zeo plasmid and used as a transfection control with β-galactosidase staining. For additional discussion of this methodology, see for example, Grentzmann et al., *RNA* 4: 479-86 (1998)].

Figure 7:
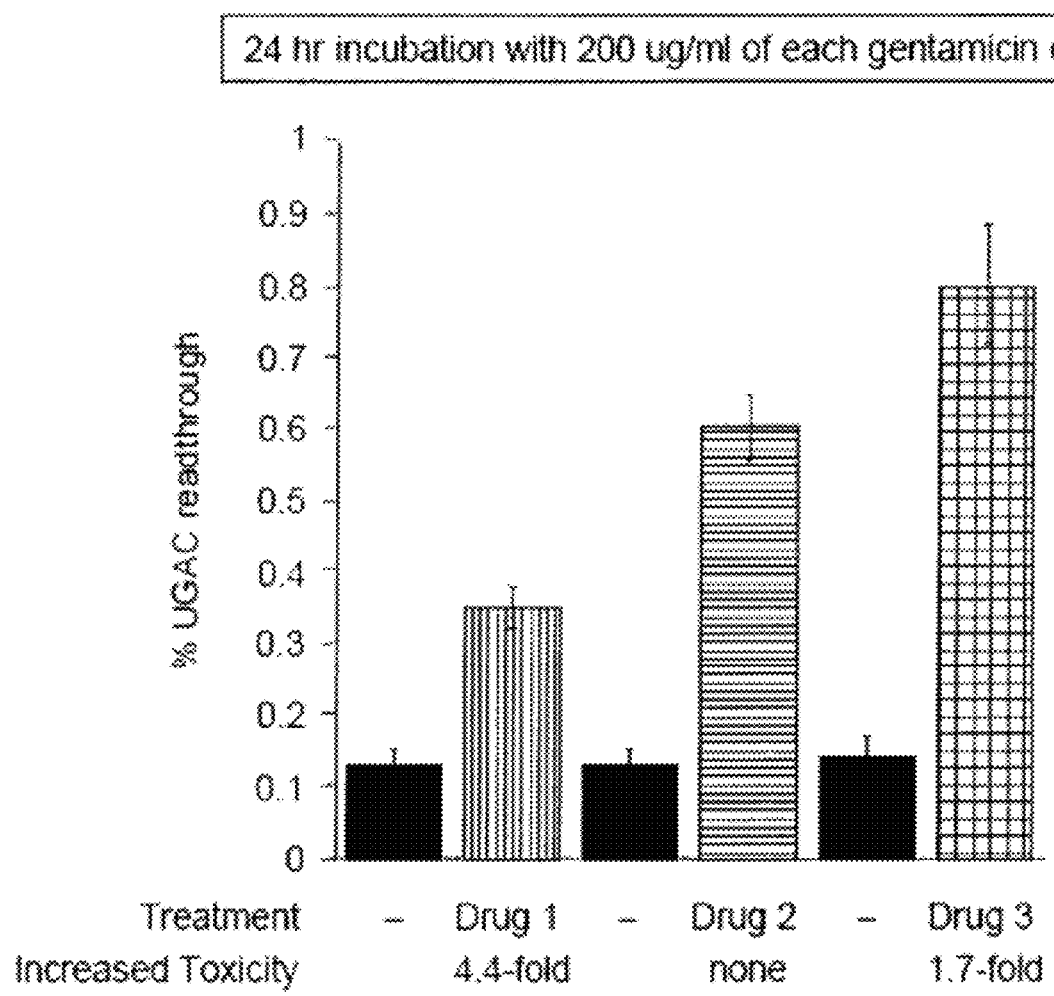
FIG. 7. A graph illustrating the effect of the C1 congener of gentamicin (labeled drug 1); the C2 congener of gentamicin (labeled drug 2); and native gentamicin on readthrough of the UGAC stop codon. The cells were exposed to 200 ug/ml of each compound for 24 hours.

The results of these tests are summarized in FIG. 7. Congener C1 exhibited minimal readthrough, C2 (drug 2) exhibited an intermediate effect on readthrough and native gentamicin exhibited the largest effect on readthrough of any of the compounds tested. FIG. 7 also includes information on the cell toxicity. Cytotoxicity was measured by comparing the number of viable cells in treated and untreated samples using a dye exclusion assay, of the compounds tested. Drug 1 (the C1 congener) was the most toxic compound tested 4.4 fold more toxic than the control (no added aminoglycoside) followed by Drug 2 (native gentamicin) 1.7 times more toxic than the control; the least toxic compound tested was Drug 2 (the C2 congener) it was no more toxic than the control.

Example 10

Proposed Clinical Trial of C2 Based Therapeutics for the Treatment of Duchenne Muscular Dystrophy In some patients with Duchenne muscular dystrophy (DMD), the disease is caused by a nonsense mutation (premature stop codon) in the gene that encodes the protein dystrophin. The C2 congener of gentamicin (Formula 1) can partially restore dystrophin production in animals with DMD due to the imposition of a premature stop codon in the gene encoding dystrophin. The main purpose of this study is to understand whether the C2 congener and derivatives thereof can safely increase functional dystrophin protein in the muscles of patients with DMD due to a nonsense mutation.

Primary outcomes criteria for the study include: Dystrophin expression as assessed by immunofluorescence evaluation of tissue obtained by biopsy of the extensor digitorum brevis (EDB) muscle of the foot Secondary Outcomes: Presence of dystrophin mRNA and dystrophin-related proteins on EDB muscle biopsy, muscle function, compliance with treatment, safety and PTC124 pharmacokinetics. Total enrollment in the study is set at least 24 patients.

In this study, patients with DMD due to a mutation that introduces a premature stop codon in into the gene encoding dystrophin are treated with C2 or a derivative thereof in a pharmaceutically acceptable form thereof. To determine if a patient qualifies for the study evaluation procedures is performed within 21 days prior to the start of treatment; these procedures include: obtaining the prospective participant's medical history; a physical examination; blood and urine tests to assess organ function; electrocardiogram (ECG); muscle biopsy for evaluation of dystrophin protein levels; and DMD-specific tests of muscle function. Eligible patients who elect to enroll in the study participate in a 28-day treatment period and a 28-day follow-up period (56 days total). The first 6 patients to enroll receive treatment with C2 at least once per day, each treatment comprises dosing each patient with about 5 mg/kg of C2 or a pharmaceutically acceptable preparation thereof. These patients are monitored over a 28-day follow-up period without treatment. Subsequently, 18 additional patients are enrolled and receive treatment with the same C2 congener; these patients are treatment at least once per day with a dose of about 10 mg/kg of C2 or a pharmaceutically acceptable preparation thereof. These patients are monitored during a 28-day follow-up period without treatment. There will be a 2-night stay at the clinical research center at the beginning and at the end of the 28 days of treatment.

To assess efficacy, patients will have an end-of-treatment biopsy and will undergo DMD-specific tests of muscle function. To assess safety and pharmacokinetics, safety assessments, blood and urine tests, and ECGs will be performed at pre-specified time points during the 28-day treatment period and the 28-day follow-up period. At the end of the 56 days, patients will be assessed periodically regarding their general health status; these evaluations will be performed by telephone contact at approximately 6-month intervals in the first 2 years and at approximately 12-month intervals in subsequent years (up to 5 years total).

All references, patents, patent applications and the like cited herein and not otherwise specifically incorporated by references in their entirety, are hereby incorporated by references in their entirety as if each were separately incorporated by reference in their entirety.

An abstract is included to aid in searching the contents of the application and it is not intended to be read as explaining, summarizing or otherwise characterizing or limiting the invention in any way.

The present invention contemplates modifications as would occur to those skilled in the art. It is also contemplated that processes embodied in the present invention can be altered, duplicated, combined, or added to other processes as would occur to those skilled in the art without departing from the spirit of the present invention.

Further, any theory of operation, proof, or finding stated herein is meant to further enhance understanding of the present invention and is not intended to make the scope of the present invention dependent upon such theory, proof, or finding.

While the invention has been illustrated and described in detail in the figures, formulas and foregoing description, the same is considered to be illustrative and not restrictive in character, it is understood that only the preferred embodiments have been shown and described and that all changes and modifications that come within the spirit of the invention are desired to be protected.

We claim:

1. A method of treating a genetic disease, comprising the steps of:
   identifying a patient, wherein the patient exhibits a pathology that includes the imposition of a stop codon in the open reading frame of an otherwise functional gene, and wherein the pathology is selected from the group consisting of Duchenne Muscular Dystrophy, cystic fibrosis, Hurler's syndrome, and Becker muscular dystrophies; and
   formulating a mixture of a therapeutically effective dose of an aminoglycoside enriched in an isolated and purified compound having the following formula, or a pharmaceutically acceptable salt thereof:

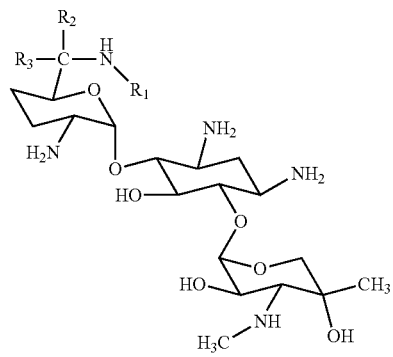

wherein, $R_1$ and $R_3$ are H, and $R_2$ is $CH_3$, and wherein the compound is present in said formulation at a level sufficient to reduce the cellular toxicity of the aminoglycoside; and administering a therapeutically effective dose of said formulation to the patient.

2. The method described in claim 1, wherein the patient is a human.

3. A method of treating genetic disease, comprising the steps of:
   identifying a patient, wherein the patient exhibits a pathology that includes the imposition of a stop codon in the open reading frame of an otherwise functional gene, wherein the pathology is selected from the group consisting of Duchenne Muscular Dystrophy, cystic fibrosis, Hurler's syndrome, and Becker muscular dystrophies, and wherein the stop codon is selected from the group consisting of: UAAC, UAGC, UGAC, UAAG, UAGG, UGAG, UAAU, UAGU, UGAU, UAAA, UAGA, and UGAA; and
   formulating a mixture of a therapeutically effective dose of an aminoglycoside enriched in an isolated and purified compound having the following formula, or a pharmaceutically acceptable salt thereof:

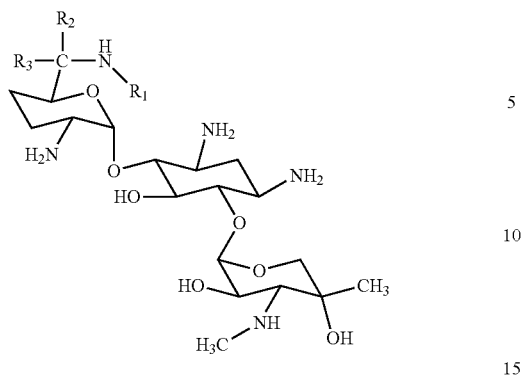
wherein, $R_1$ and $R_3$ are H, and $R_2$ is $CH_3$, and wherein the compound is present in said formulation at a level sufficient to reduce the cellular toxicity of the amino glycoside; and administering a therapeutically effective dose of said formulation to the patient.
4. The method according to claim 3, wherein the stop codon is UAGC.
* * * * *